United States Patent [19]

Sandler

[11] Patent Number: 4,944,853

[45] Date of Patent: Jul. 31, 1990

[54] PHOTOCHEMICAL PREPARATION OF 3-(ORGANOTHIO) ALDEHYDES

[75] Inventor: Stanley R. Sandler, Springfield, Del.

[73] Assignee: Pennwalt Corporation, Philedelphia, Pa.

[21] Appl. No.: 405,784

[22] Filed: Sep. 11, 1989

[51] Int. Cl.$^5$ .............................................. B01J 19/08
[52] U.S. Cl. ......................... 204/157.76; 204/157.78; 204/157.93
[58] Field of Search ...................... 204/157.76, 157.78, 204/157.93

[56] References Cited

U.S. PATENT DOCUMENTS 3,529,940  9/1970  Shima et al. .......................... 23/288

FOREIGN PATENT DOCUMENTS 276380    12/1954  Japan .
40-19090   8/1965  Japan .
1336541   11/1973  United Kingdom .

OTHER PUBLICATIONS

Yamada et al.,—"Applications of Ion Exchange Resins in Organic Reactions", Jour. of Pharm. Soc., Japan (1953) (Translation copy only).

Szabo et al., "Reactions of Mercaptans with Unsaturated Compounds", Jour. Amer. Chem. Soc., 70, 3667 (1948).

Hall et al., "Reactions of Crotonaldehyde with Ethanethiol", Jour. Chem. Soc., 2723 (1949).

Yamagishi, "Studies of Photochemical Addition Reactions", Part 5 [1], Addition Reactions of Crotonaldehyde, Methyl Vinyl Ketone and Cinnamaldehyde, Nippon Kagaku Zasshi (Bull. Chem. Soc. Japan), vol. 80, pp. 764–766, 1959 (Japanese Text—English Translation).

Primary Examiner—John F. Niebling
Assistant Examiner—Ben C. Hsing

[57] ABSTRACT

A process is disclosed for the preparation of 3-(organothio)aldehydes by reacting a mercaptan with an $\alpha, \beta$-unsaturated aliphatic aldehyde under actinic radiation in the absence of an oxygen-containing gas wherein the mercaptan and aldehyde are mixed in substantially equimolar amount and the reaction temperature ranges from about 2° to less than 60° C.

10 Claims, No Drawings

PHOTOCHEMICAL PREPARATION OF 3-(ORGANOTHIO) ALDEHYDES

BACKGROUND OF THE INVENTION

This invention relates to a process of preparing 3-(organothio)aldehydes in a reaction of an essentially equimolar mixture of a mercaptan and an unsaturated aliphatic aldehyde by subjecting the reactants to actinic radiation within a specified temperature range and in the absence of an oxygen-containing atmosphere.

The products of the process of this invention are used, for example, as intermediates for the preparation of pesticides and antioxidants and as odorant or flavoring agents.

PRIOR ART

It is known to prepare 3-(ethylthio)butanol using a photochemical process [K. Yamagishi, Nippon Kagaku Zasshi (Bull. Chem. Soc., Japan) 80,764 (1959)]. The previously disclosed photochemical (U.V) process involves the reaction of 3.0 moles of ethyl mercaptan with 1.0 mole of crotonaldehyde over a 3 hour period without controlling the temperature. This process results in only an 18% yield of the desired product, 3-(ethylthio)-butanal, and a 37% yield of the diethyl mercaptal of crotonaldehyde [$CH_3CH=CH-CH(SC_2H_5)_2$]. The reference also reported that when the reaction was carried out in a stream of nitrogen gas, the yield was low.

STATEMENT OF THE INVENTION

The present invention is a process for the preparation of 3-(organothio)aldehydes which comprises (a) forming an essentially equimolar mixture of a $C_1$–$C_{12}$ alkyl, a $C_5$–$C_6$ cycloalkyl or a $C_6$–$C_{12}$ aryl or alkaryl mercaptan with a $C_3$–$C_{10}$ $\alpha,\beta$-unsaturated aliphatic aldehyde an (b) subjecting said mixture to actinic radiation at a temperature ranging from about 2° C. to less than 60° C. in the absence of an oxygen-containing atmosphere to thereby produce a product consisting predominantly of the corresponding 3-(organothio) aldehyde.

DETAILED DESCRIPTION OF THE INVENTION

This invention concerns a process for the preparation of 3-(organothio) aldehydes. More preferably, it involves the preparation at high yields of 3-($C_1$–$C_{12}$ alkyl thio, $C_5$–$C_6$ cycloalkylthio, or $C_6$–$C_{12}$ aryl or alkaryl thio) $C_3$–$C_{10}$ alkanals from substantially equimolar amounts of the corresponding mercaptans and $\alpha,\beta$-unsaturated aldehydes under the influence of actinic radiation and a temperature within a prescribed range.

The process described herein produces compounds of the formula

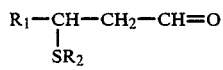

where $R_1$ is hydrogen or $C_1$–$C_7$ alkyl and $R_2$ is a $C_1$–$C_{12}$ alkyl, a $C_5$–$C_6$ cycloalkyl or a $C_6$–$C_{12}$ aryl or alkaryl radical.

The alkyl and cycloalkyl mercaptans useful in this invention include, without limitation, methyl, ethyl, n-propyl, isopropyl, n-butyl, t-butyl, n-pentyl, t-amyl, n-hexyl and cyclohexyl mercaptan. The aryl and alkaryl mercaptans include, for example, phenyl, tolyl, xylyl, benzyl and p-chlorophenyl. The preferred mercaptans are the $C_1$–$C_8$ alkyl mercaptans and most preferably methyl and ethyl mercaptan.

The $C_3$–$C_{10}$ $\alpha,\beta$-unsaturated aliphatic aldehydes useful in this invention include, for example, acrolein, crotonaldehyde, 2-pentenal, and 2-hexanal. The preferred aldehydes are $C_3$–$C_6$ $\alpha,\beta$-unsaturated alkanals, most preferably crotonaldehyde and acrolein.

The photolytic reaction is carried out within a temperature range of about 2° C. to less than 60° C., preferably from about 2° C. to about 20° C. The reaction may be initiated in air but is essentially carried out in the absence of an oxygen-containing gas and preferably under a blanket of an inert gas such as argon, helium, neon or nitrogen. The most preferred gas is nitrogen. The process is usually operated at atmospheric or slightly elevated pressure but can also be carried out at super-atmospheric pressure up to that which the reactor will withstand.

Any type of actinic radiation can be used in the photochemical reaction, but a reactor equipped with an ultraviolet (U.V.) light source is preferred. The U.V. light source will, preferably, have U.V. emission spectra ranging from above 160 nanometers (nm) to at least 400 nm. The lamp employed in the following examples had a 450 watt high pressure Hanovia lamp with a broad range of U.V. spectral bands including 25.6 watts at 366 nm. and 13.2 watts at 313 nm. Examples of lamps emitting in the prescribed range are deuterium lamps, low-pressure mercury-argon lamps, high-energy xenon flash lamps and high pressure mercury (Hanovia) lamps as mentioned above.

Photoinitiators including, for example, acetophenone, acetophenone derivatives and Vicure 10 (benzoin alkyl ether), a product of Stauffer Chemical Co., in amounts of from 0.01 to 2% based on the aldehyde, are frequently useful when added to the reactants of the process.

The critical feature of the invention is the use of an essentially equimolar solution of the reactants at the onset of the photolytic process. It was determined that starting the reaction with a slight excess of the mercaptan equimolar solution (1.0–1.1 moles mercaptan to 1.0 moles unsaturated aldehyde, for example) results in a product containing a low amount of by-product, for example, diethyl mercaptal. When one of the reactants was added gradually to the total amount of the other, a large percentage of by-product was obtained.

EXAMPLES

The following examples illustrate this invention. Gas chromatography (GC) was used to determine the amount of the 3-(ethylthio) butanal and the diethyl mercaptal of crotonaldehyde produced in the reaction.

EXAMPLE 1

The photochemical reactor assembly used consisted of a 500-ml borosilicate reactor, quartz immersion well, sparger tube (nitrogen), Teflon stirring bar, thermometer and 450-watt Hanovia high-pressure mercury lamp attached to a power supply. Ethyl mercaptan (3.0 moles) and crotonaldehyde (3.0 moles) were added to the reactor all at once. The resulting solution was cooled to about 2° C. to 20° C., photolyzed while a slow stream of nitrogen was passed into the reactor and the temperature range maintained. Samples were withdrawn periodically and the composition checked by GC as shown below (balance is mainly unreacted ethyl mercaptan and crotonaldehyde).

| Time of Reaction (U.V) (Minutes) | GC % Area 3-(Ethylthio)- Butanal | Diethyl Mercaptal of Crotonaldehyde |
| --- | --- | --- |
| 35 | 39.5 | 0.7 |
| 80 | 37.3 | 0.4 |
| 270 | 52.3 | 0.3 |
| 360 | 55.2 | 0.3 |

EXAMPLE 2

The same reactor as set forth in Example 1 was charged with crotonaldehyde (3.0 moles). Ethyl mercaptan (3.0 moles) was, thereafter, slowly added to the crotonaldehyde at a reactor temperature of 45°-56° C. Photolysis was carried out under nitrogen, as reported in Example 1, while the temperature was maintained. As shown below, with this procedure, a large proportion of the diethyl mercaptal is formed.

| | GC Analysis, % Area | | |
| --- | --- | --- | --- |
| % Ethyl Mercaptan Added | Time of Photolysis (Minutes) | 3-(Ethylthio) Butanal | Diethyl Mercaptal of Crotonal- dehyde |
| 20 | 5 | 10.5 | 20.7 |
| 100 | 45 | 24.2 | 36.8 |

The reaction mixture was cloudy and water droplets were present on the walls of the reactor.

EXAMPLE 3

The photochemical reactor assembly used for this example is a synthetic silica-glass vessel suitable for use in a continuous process in the liquid phase under pressure and having associated known equipment for introducing and cooling reactants, purging the reactor and separating products therefrom. The U.V. light source is a 550-watt, high pressure mercury lamp having an emission spectrum from below 222 nm to over 1360 nm. The system is purged with nitrogen and a mixture of equimolar amounts of liquified methyl mercaptan and acrolein is charged to the reactor, cooled to 2°-20° C. and photocatalyzed under nitrogen at a pressure of 150 psig. Samples of the product ar periodically withdrawn and subjected to GC analysis. The product is 3-(methylthio) propanal with a low level of by-product dimethyl mercaptal and a minor amount of unreacted methyl mercaptan and acrolein.

I claim:

1. A process for the preparation of 3-(organothio) aldehydes comprising (a) forming an equimolar mixture of a $C_1$-$C_{12}$ alkyl, a $C_5$-$C_6$ cycloalkyl or a $C_6$-$C_{12}$ aryl or alkaryl mercaptan with a $C_3$-$C_{10}$ $\alpha$, $\beta$-unsaturated aliphatic aldehyde, and (b) subjecting said mixture to actinic radiation at a temperature ranging from about 2° to less than 60° C. in the absence of an oxygen-containing atmosphere to thereby produce a product consisting predominantly of the corresponding 3-(organothio) aldehyde.

2. The process of claim 1 wherein the temperature ranges from about 2° C. to about 20° C.

3. The process of claim 1 wherein the alkyl mercaptan is $C_1$ to $C_8$ alkyl mercaptan.

4. The process of claim 1 wherein the unsaturated aliphatic aldehyde is a $C_3$-$C_6$ alkanal.

5. The process of claim 1 carried out under an inert gas.

6. The process of claim 5 wherein the inert gas is nitrogen.

7. The process of claim 5 wherein the mercaptan is methyl or ethyl mercaptan, the aldehyde is crotonaldehyde or acrolein, and the temperature ranges from about 2° to about 20° C.

8. The process of claim 1 wherein the mercaptan is ethyl mercaptan and the aldehyde is crotonaldehyde.

9. The process of claim 1 wherein the mercaptan is methyl mercaptan and the aldehyde is acrolein.

10. The process of claim 1 wherein the actinic radiation is a light source having an ultraviolet emission spectrum ranging from above 160 nm up to at least 400 nm.

* * * * *